United States Patent
Bharmi

(10) Patent No.: US 7,539,539 B1
(45) Date of Patent: May 26, 2009

(54) IMPLANTABLE CARDIAC STIMULATION DEVICE WITH RESPIRATORY MODULATED THERAPY DELIVERY

(75) Inventor: Rupinder Bharmi, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 498 days.

(21) Appl. No.: 11/248,888

(22) Filed: Oct. 11, 2005

(51) Int. Cl.
*A61N 1/365* (2006.01)
*A61B 5/08* (2006.01)

(52) U.S. Cl. ............... 607/20; 607/17; 607/19; 607/42; 600/529

(58) Field of Classification Search ............ 607/17, 607/19, 20; 600/484, 532
See application file for complete search history.

(56) References Cited

U.S. PATENT DOCUMENTS

| | | | |
|---|---|---|---|
| 6,141,590 A * | 10/2000 | Renirie et al. ............ | 607/20 |
| 6,512,949 B1 | 1/2003 | Combs et al. ............ | 600/547 |
| 6,904,320 B2 * | 6/2005 | Park et al. ............... | 607/17 |
| 2004/0181260 A1 | 9/2004 | Anderson et al. ......... | 607/17 |
| 2004/0186523 A1 | 9/2004 | Florio ..................... | 607/17 |

FOREIGN PATENT DOCUMENTS

EP    1 459 785 A1    9/2004

* cited by examiner

*Primary Examiner*—Carl H Layno
*Assistant Examiner*—Natasha N Patel

(57) ABSTRACT

A method of providing cardiac stimulation therapy and a device for providing the therapy. A patient's cardiac activity as well as cyclical respiration is monitored. Cardiac stimulation is provided as indicated as therapeutic intervention for a variety of cardiac arrhythmias according to variable timing parameters. One or more of the timing parameters under which cardiac pacing stimulations are provided is varied or modulated with the cyclical variations in respiration. The one or more timing parameters are generally shortened or elongated in concert with the alternating inspiration/exhalation phases of respiration. In certain implementations, the patient's respiration is inferred from cardiac based physiologic signals. The methods and devices for providing cardiac stimulation therapy more accurately emulate natural healthy physiologic activity.

8 Claims, 10 Drawing Sheets

IMPLANTABLE CARDIAC STIMULATION DEVICE WITH RESPIRATORY MODULATED THERAPY DELIVERY

FIELD OF THE INVENTION

The invention relates to the field of implantable cardiac stimulation devices and, more particularly, to devices having operating parameters which are rhythmically modulated based at least partly on respiration phase.

BACKGROUND OF THE INVENTION

Implantable cardiac stimulation devices have been developed to treat a wide variety of patient cardiac arrhythmias. Implantable cardiac stimulation devices typically include an implantable battery-powered stimulation pulse generator and microprocessor-based controller which are encased in a biocompatible housing. One or more sensing/stimulation electrodes are typically positioned in contact with corresponding cardiac tissue and are interconnected via one or more implantable leads with the controller and stimulation pulse generator. The device monitors the physiological condition of the patient and selectably provides therapeutic stimulations when indicated to attempt to restore desired cardiac function.

Simpler devices may monitor and/or treat only a single chamber of the patient's heart, whereas more sophisticated devices are capable of sensing and delivering therapy to multiple chambers and may be referred to as dual or multi-chamber devices. As one example of the capabilities of such devices, a multi-chamber device can be capable of sensing the activity in both a patient's atrium and ventricle, as well as delivering independent therapy to one or more of the chambers when indicated. The timing of stimulation delivery is generally controlled by the device's controller as a function of both sensed intrinsic events as well as evoked or stimulated cardiac activity. The timing of therapy delivery is typically controlled to accommodate refractory periods following depolarization events as well as to accommodate and synchronize the activity of the multiple chambers of the heart to improve the pumping performance or hemodynamic characteristics of the heart.

As one particular example, many multi-chamber devices are capable of monitoring ventricular activity and providing therapeutic stimulation to the ventricle based on activity in the corresponding atrium. For example, such devices may be capable of monitoring the occurrence of an intrinsic depolarization in an atrium or alternatively tracking the delivery of a therapeutic stimulation to the atrium and then subsequently monitoring the activity of the corresponding ventricle and delivering a subsequent ventricular stimulation if an intrinsic ventricular depolarization does not occur within an indicated time window. This time window is generally referred to as an atrio-ventricular (AV) delay and marks a duration following either of an intrinsic atrial depolarization or an evoked or stimulated atrial depolarization at the end of which a ventricular stimulation will be provided if an appropriate intrinsic or AV conducted depolarization does not occur. In certain cases, the AV delay is programmed to a fixed value and in other cases is variable based on the heart rate which the device is currently seeking to maintain.

A desirable feature of implantable cardiac stimulation devices is that they be capable of dynamically accommodating variations in the patient's metabolic need. For example, implantable devices may be capable of tracking or monitoring a patient's activity level and adjusting one or more operating parameters of the device, such as a heart rate which the device maintains, to correspond with the changes in the patient's metabolic need. Such devices are generally referred to as rate responsive devices. Thus, in certain cases, rate responsive devices can vary other operating parameters of the device, such as an AV delay, with changes in a heart rate which the device maintains. In a normal healthy person, a variety of physiological feedback mechanisms act to adjust the function of a variety of physiological processes, including cardiac activity, to track ongoing changes in the person's status, such as activity level, periods of sleep or rest, physical and/or emotional stress, etc. A difficulty arises, however, with patients having impaired health, for example patients for whom an implantable cardiac stimulation device is indicated. More particularly, certain feedback or automatic control mechanisms which are generally intact in the normal healthy person are either not well understood or have proven difficult to replicate with an implantable device, particularly when the device is assuming a significant proportion or complete control of the patient's cardiac activity.

SUMMARY OF THE INVENTION

Thus, it will be appreciated that there is a continuing ongoing need for improved methods of delivering therapy to a patient as well as improvements in devices providing such therapy to more closely emulate a normal healthy condition. In particular, there is a desire for the ability to more accurately dynamically adjust the operating parameters of an implantable cardiac stimulation device to more accurately mimic healthy physiologic activity.

Certain embodiments of the invention are based at least partially on the conclusion that hemodynamic advantage may be realized by more accurately maintaining intrinsic conduction when providing multi-chamber based therapy. Certain embodiments are also at least partially based on the goal of providing rate adaptive AV delays where intrinsic AV conduction is absent for improved hemodynamic performance. Certain other embodiments are based at least partially on observations of cyclical variations in the relative timing or other characteristics of a variety of cardiac parameters or characteristics in concert with the cyclical inspiration and expiration phases of respiration and provides methods and systems for modulating one or more operating parameters of an implantable device, such as an AV delay, to track these intrinsic cyclical variations. Certain implementations more closely mimic respiratory sinus arrhythmia (RSA) with therapy provided by an implantable device.

Thus, one embodiment includes a method of delivering cardiac therapy comprising providing cardiac stimulation therapy to a patient at a determined rate with delivery of stimulation being provided according to one or more operating parameters, monitoring the patient's respiration, determining a current phase of the patient's respiration, and setting at least one of the stimulation operating parameters based on the determined current respiration phase.

Another embodiment includes an implantable cardiac stimulation device comprising an implantable stimulation pulse generator, at least one implantable stimulation electrode connected to the stimulation pulse generator, at least one implantable sensing electrode arranged to sense cardiac activity, and a controller receiving physiological signals from the at least one sensing electrode wherein the controller is in communication with the pulse generator so as to selectively induce the pulse generator to provide indicated therapeutic cardiac stimulations via the at least one stimulation electrode according to one or more therapy parameters wherein at least one of the parameters is modulated on a cardiac beat-by-beat basis in synchrony with a respiration pattern.

A further embodiment includes an implantable cardiac stimulation device comprising means for sensing cardiac activity, means for sensing respiration, means for generating and delivering stimulation to patient tissue, and means for controlling in communication with the means for sensing cardiac activity, the means for sensing respiration, and the means for generating and delivering stimulation, wherein the means for controlling monitors the sensed cardiac activity and determines indications for delivery of therapy and monitors the means for sensing respiration and determines a current phase of the respiration and determines parameters under which the means for controlling induces the means for generating and delivering stimulation to deliver therapy based at least in part on the determined current respiration phase. These and other objects and advantages of the invention will become more apparent from the following description taken in conjunction with the accompanying drawings.

BRIEF DESCRIPTION OF THE DRAWINGS

FIGS. 3A-3C illustrate intrinsic variations in particular aspects of sinus activity with vagal influences throughout respiration cycles wherein FIG. 3A is a graph of variation in R-R interval over time;
FIG. 3B is a graph of variation in AV delay over time; and
FIG. 3C is a graph of variation in P-P interval over time.

DETAILED DESCRIPTION OF THE PREFERRED EMBODIMENT

Reference will now be made to the drawings wherein like numerals refer to like parts throughout. The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
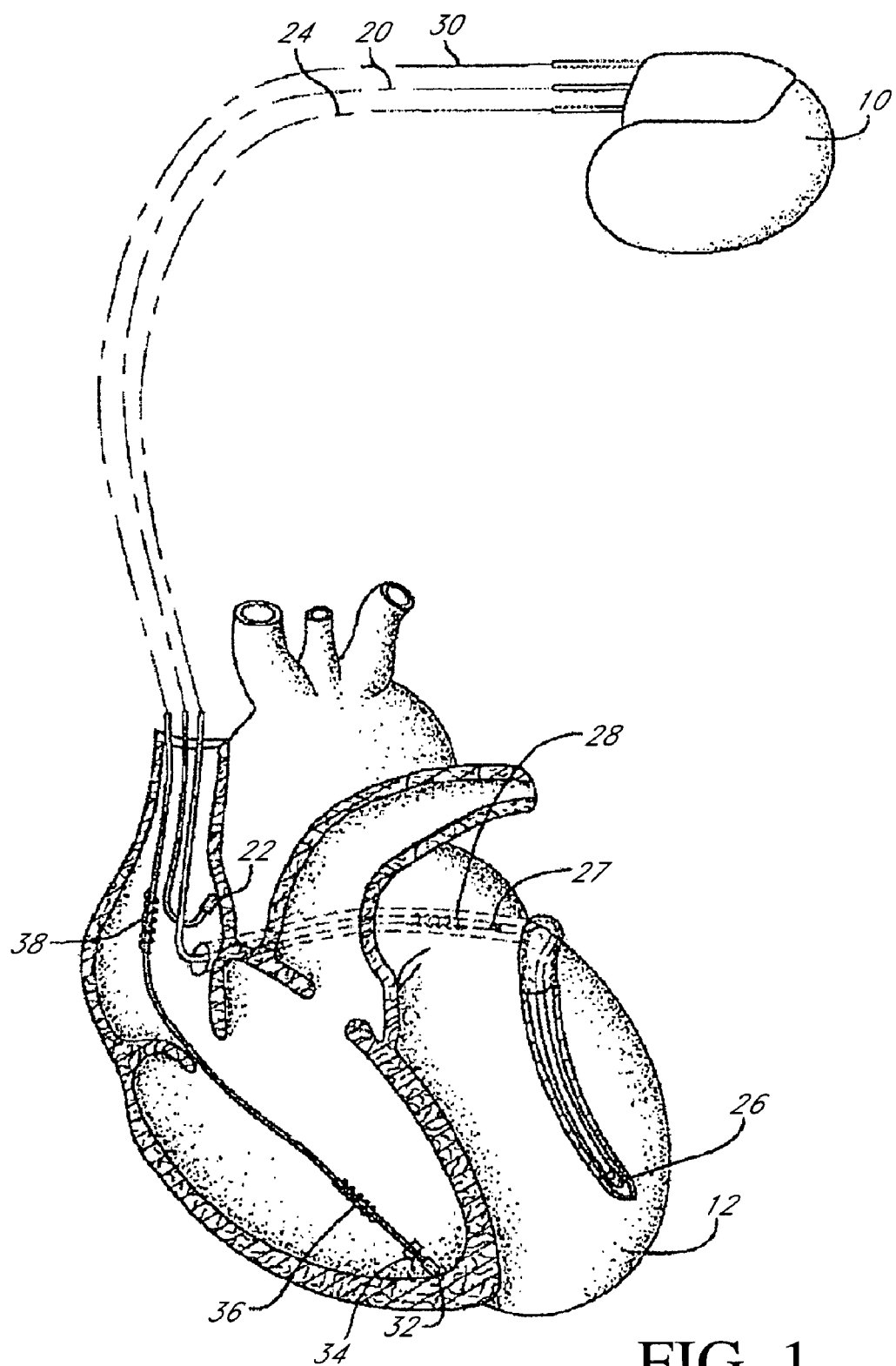
FIG. 1 is a simplified diagram illustrating an implantable stimulation device in electrical communication with at least three leads implanted into a patient's heart for delivering multi-chamber stimulation and shock therapy.

In one embodiment, as shown in FIG. 1, a device 10 comprising an implantable cardiac stimulation device 10 is in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
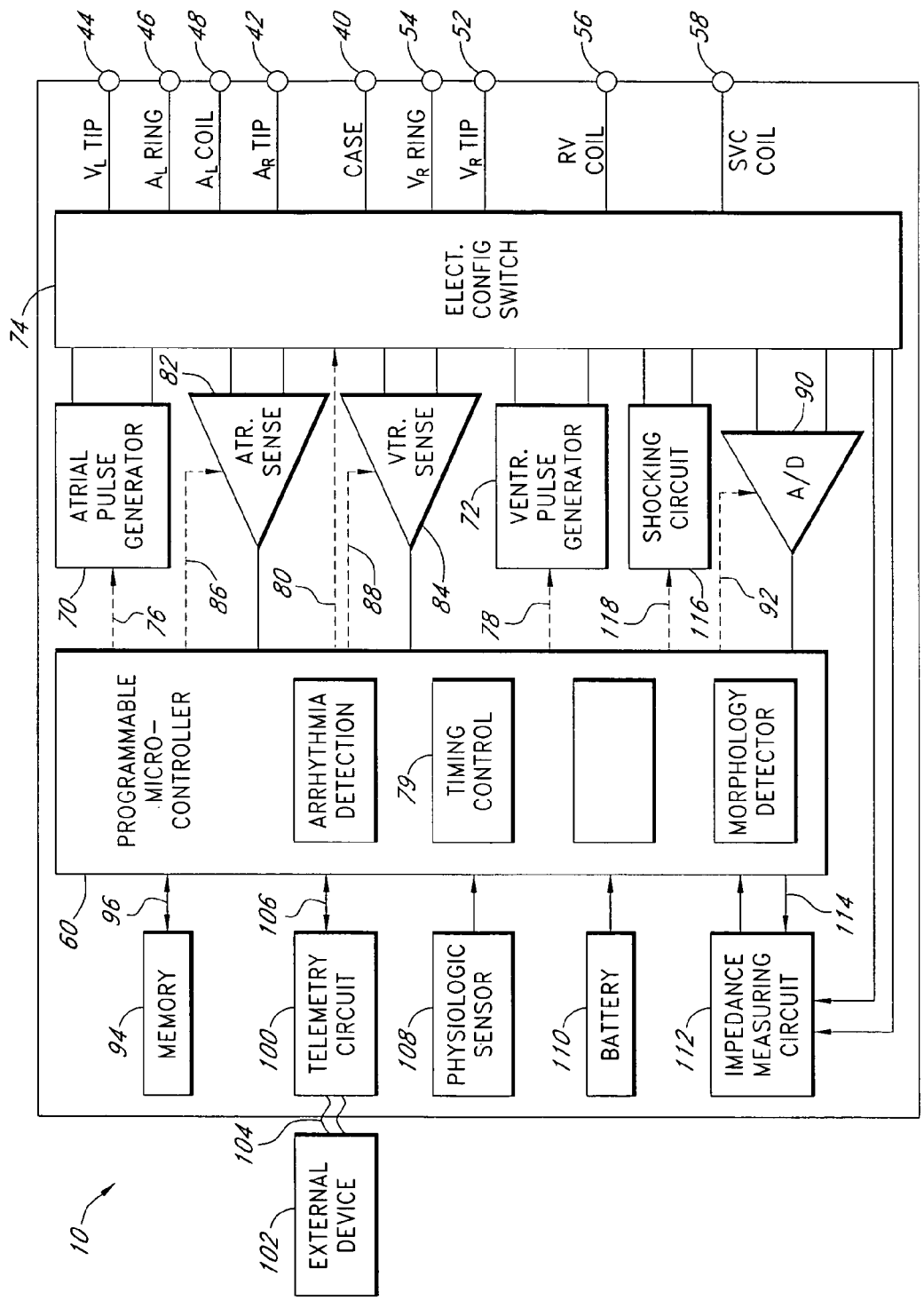
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independently of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram (IEGM) signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows IEGMs and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5-10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Certain aspects of the invention are based at least in part on an analysis of observations made by others of patients under various conditions. This analysis is at least partially motivated by a desire to more closely track delivery of cardiac stimulation therapy to natural physiological processes. More particularly, observations have been made of patients in which AV delays were varied to substantially preserve intrinsic conduction and compared to results where AV delay was varied to produce ventricular pacing. A control group of five patients having chronic AV block were also observed for the effects of a rate adaptive AV delay as compared to a fixed AV delay. During the observations, paired T testing showed a significantly lower peak oxygen volume ($VO_2$) (P less than 0.015) and oxygen pressure ($O_2P$) (P less than 0.01) in patients with atrially tracked ventricular pacing as compared to intrinsic AV conduction. In contrast, the control group exhibited a significant improvement in peak $O_2$ volume $VO_2$ with rate adaptive AV delay as compared to fixed AV delay programming (P less than 0.05).

Figure 3A:
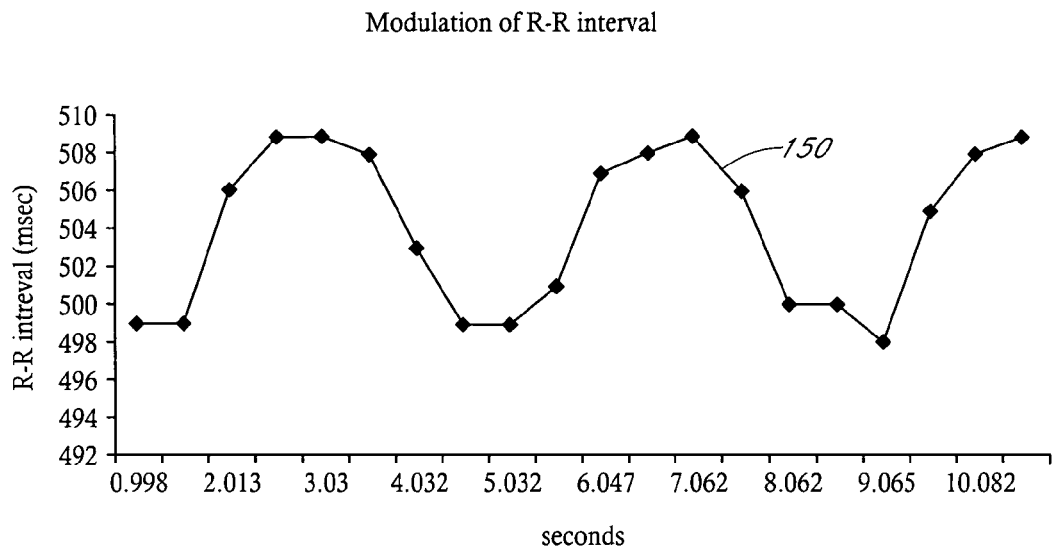
Figure 3B:
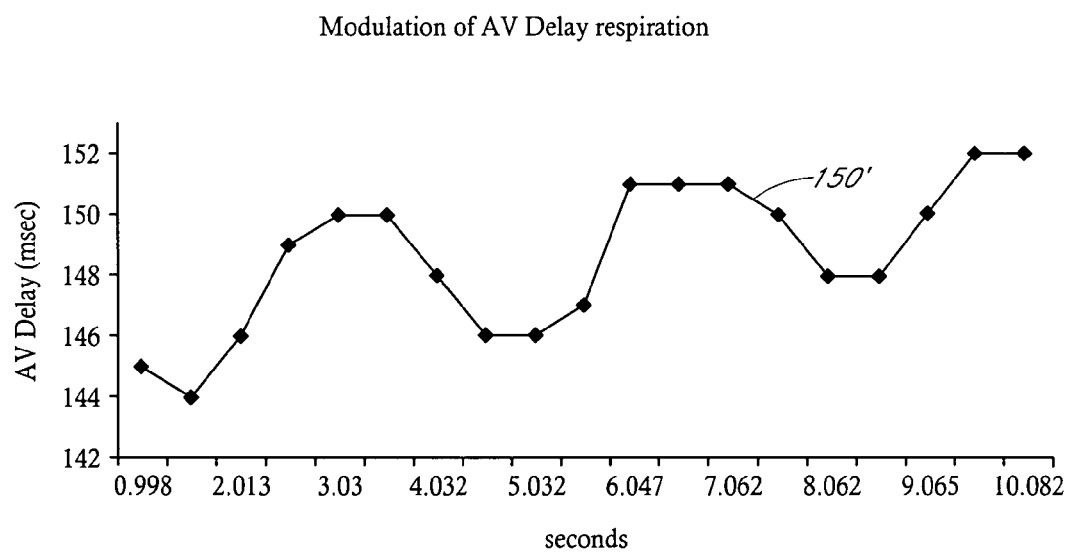
Figure 3C:
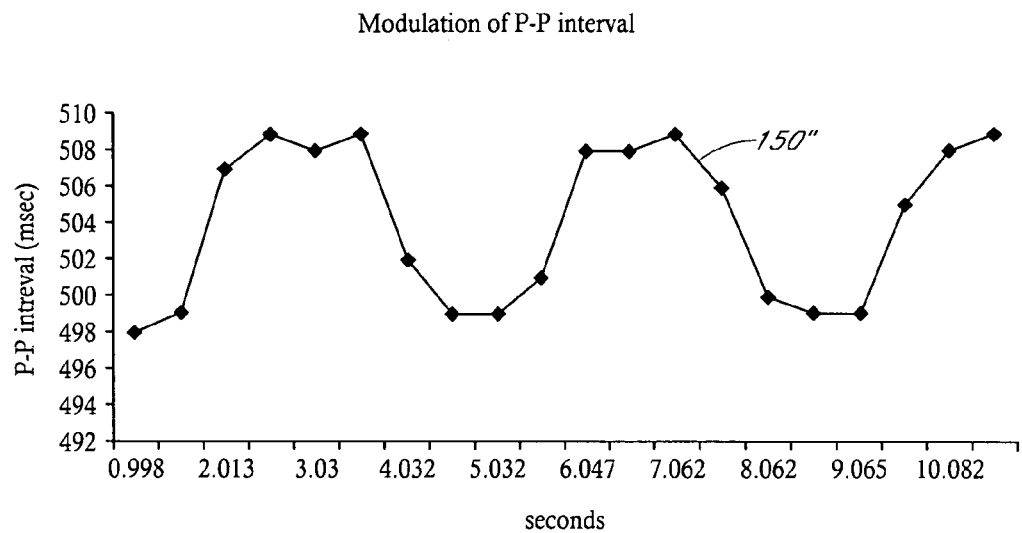

FIGS. 3A, 3B and 3C illustrate observed variations over time in various cardiac timing characteristics 150 over time corresponding to the patient's respiration cycle. More particularly, FIG. 3A illustrates variations in a first cardiac timing characteristic 150 corresponding in this embodiment to the RR interval or time interval between consecutive ventricular depolarizations. In this embodiment, the first cardiac timing characteristic 150 corresponding to R-R interval reaches peaks during periods of respiration exhalation phases of approximately 508 to 510 milliseconds. The first cardiac timing characteristic 150 similarly reaches shorter or depressed intervals of approximately 498 to 500 milliseconds substantially coincident with inhalation phases of the respiration cycle.

FIGS. 3B and 3C illustrate second cardiac timing characteristics 150' and third cardiac timing characteristics 150" corresponding in this embodiment to variations in AV delay and P-P interval or interval between consecutive atrial events. Both the second cardiac timing characteristics 150', as shown in FIG. 3B, and the third cardiac timing characteristics 150", as shown in FIG. 3C, exhibit similar variations or modulations substantially tracking the cyclical expiration and inspiration phases of the subject's respiration.

Figure 4:
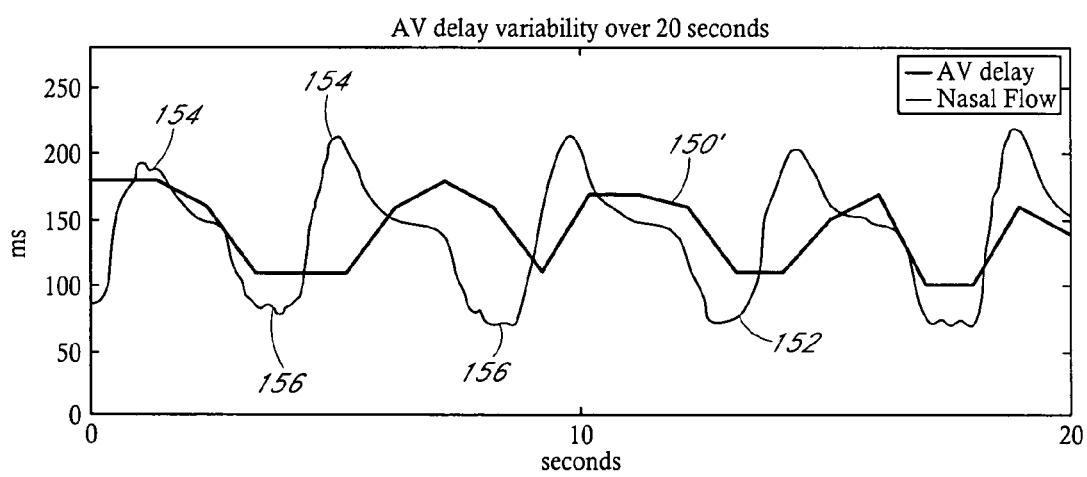
FIG. 4 illustrates variations in AV delay over a 20 second period with influence from the varying vagal tone and respiratory phase as indicated by nasal flow.

FIG. 4 illustrates another embodiment of variations in the second cardiac timing characteristic 150' corresponding in this embodiment to AV delay as compared to cyclical respiration flow 152. FIG. 4 illustrates these variations over a more extended period of time, in this embodiment over approximately 20 seconds or approximately 4½ respiration cycles. In this embodiment, the frequency of variation or modulation is approximately 0.2 Hz corresponding to the breathing frequency. The respiration flow 152 exhibits local peaks corresponding to the exhalation phase indicated as 154 with interposed troughs or local minima corresponding to the cyclical inhalation phases 156.

It can be seen that the second cardiac timing characteristic 150' (in this embodiment comprising AV delay) also exhibits local peaks and troughs which closely track the local peaks and troughs of the exhalation and inhalation phases 154, 156 of the patient's cyclical respiration. FIG. 4 illustrates that the intrinsic or naturally occurring variation or modulation in the delay of AV conduction naturally varies in a cyclical manner, increasing and decreasing substantially in concert with exhalation and inhalation phases 154, 156 of respiration. Thus, certain embodiments of the invention have the goal of more accurately mimicking or emulating this natural intrinsic behavior by varying one or more cardiac timing characteristics 150 or other operational parameter, particularly in applications wherein one or more aspects of intrinsic activity are either at least partially absent or overridden by therapy provided by the device 10. FIG. 4 illustrates a particularly reliable and accurate indicator of the cyclical respiration, in this embodiment a respiration flow 152 comprising a measured nasal flow. In certain other implementations, a directly measured respiration flow 152 may be difficult or impractical to implement and indirect measures of respiration can be employed.

Figure 5:
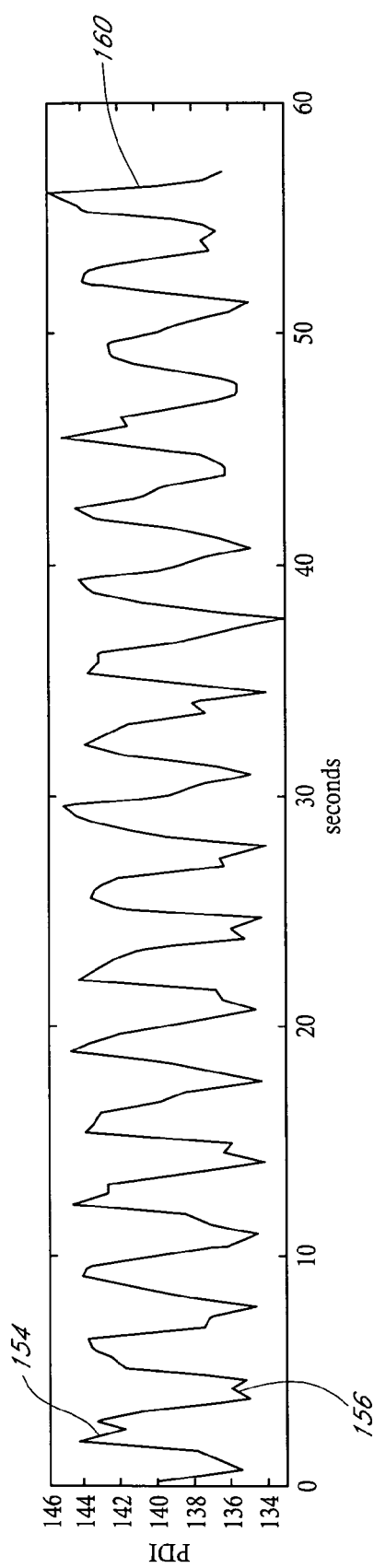
FIG. 5 illustrates one embodiment of a cardiac based surrogate indicator for respiration cycle.
Figure 6:
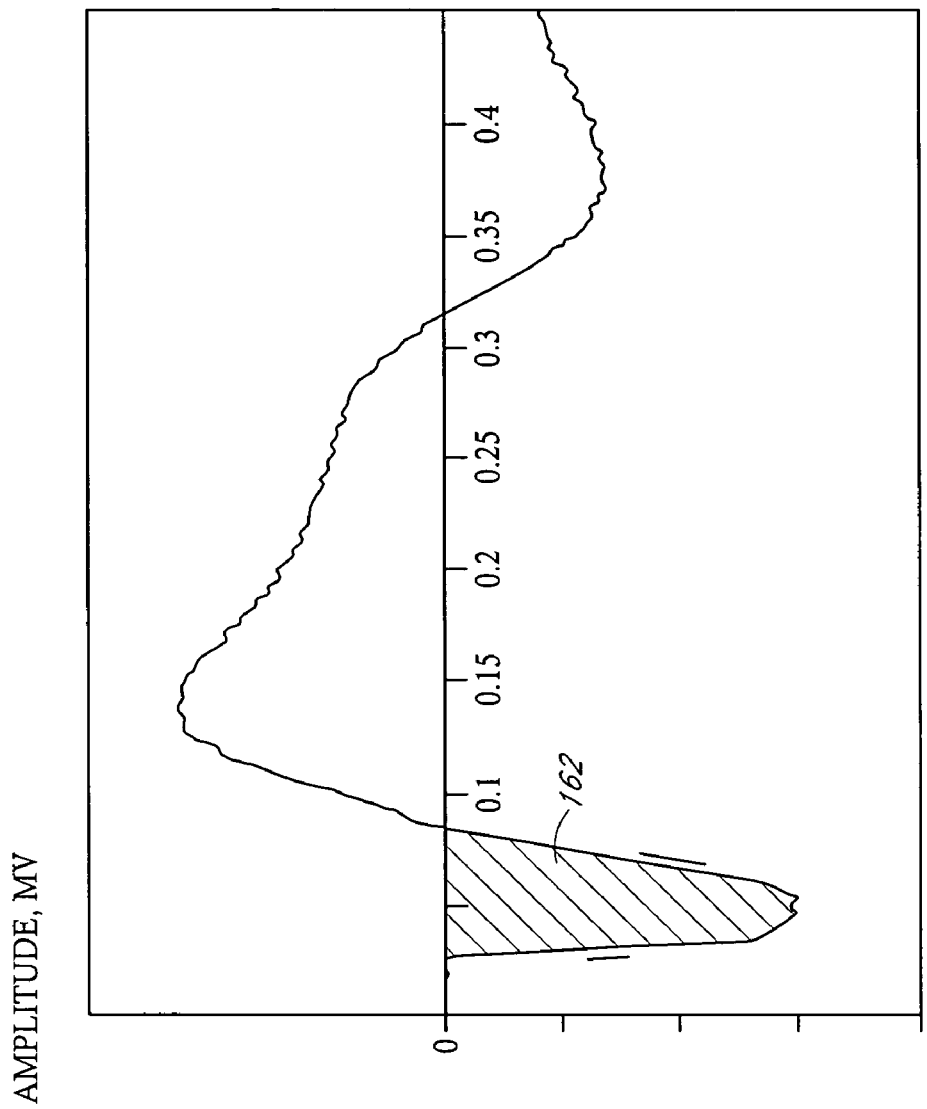
FIG. 6 illustrates one embodiment of a cardiac based indicator comprising a paced depolarization integral (PDI).

FIGS. 5 and 6A, 6B, and 6C illustrate various embodiments of alternative measures indicative of the subject's respiration. More particularly, FIG. 5 illustrates a first cardiac based respiration indicator 160 which provides time varying signals indicative of the subject's respiration cycle. In this embodiment, the first cardiac respiration indicator 160 comprises a paced depolarization integral (PDI) 162. As illustrated in FIG. 6 in greater detail, the PDI 162 corresponds to an integral of one evoked ventricular depolarization response. The PDI 162 provides advantages for use as the first cardiac-based respiration indicator 160 as the PDI 162 is already gathered and utilized for other functions in the device 10, such as for auto capture functions. Thus, in certain embodiments, obtaining the PDI 162 for use as the first cardiac-based respiration indicator 160 does not impose additional measurement overhead costs on the device 10 as the measure is already existent.

As can be seen in FIG. 5, in this embodiment, the first cardiac-based respiration indicator 160 comprising a plurality of PDI 162 measurements performed over time exhibits a cyclical variation having peaks corresponding to the exhalation phase 154 of respiration with interposed local minima or troughs corresponding to the inhalation phases 156 of the patient's respiration. In this particular embodiment, the first cardiac-based respiration indicator 160 oscillates about a mean of approximately 140 with variations of approximately ±5 or ± approximately 3.6%. Thus, the first cardiac-based respiration indicator 160 can be readily evaluated to identify the exhalation and inhalation phases 154, 156, such as by local maxima and minima peak detectors as well as a variety of other systems and methods for determining fiducial or monument data points from a time varying signal wave form well known to those of ordinary skill.

Figure 7A:
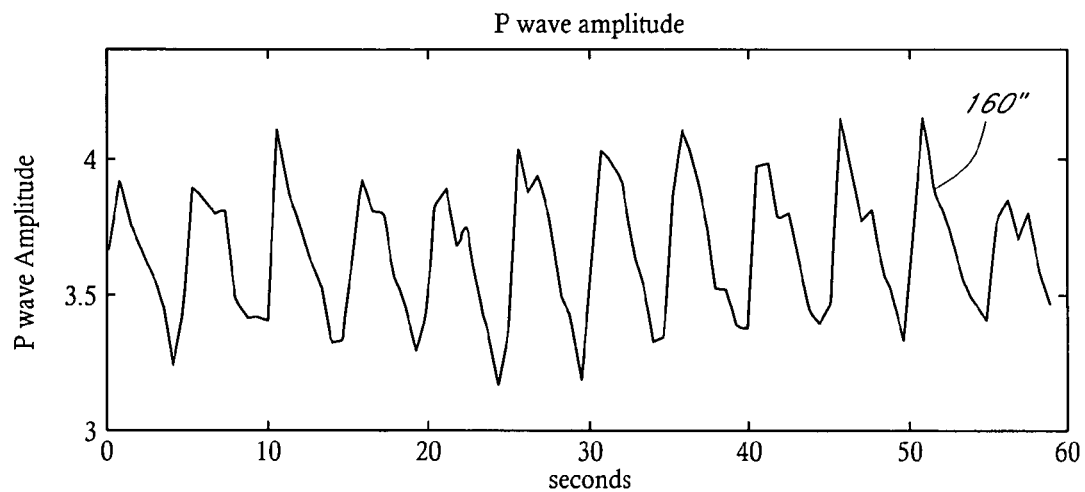
FIGS. 7A, 7B, and 7C illustrate alternative embodiments of cardiac based surrogate indicators for respiration cycle.
Figure 7B:
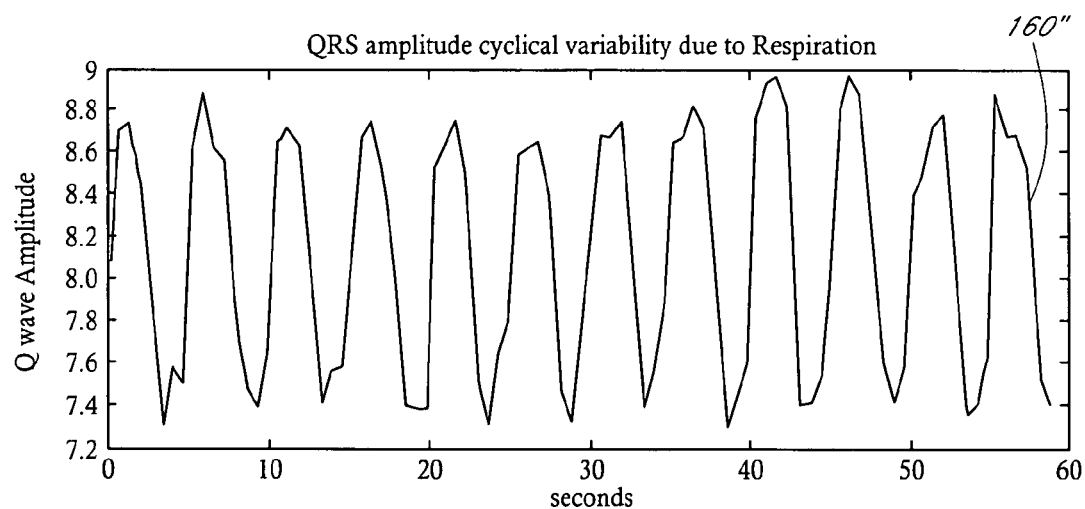
Figure 7C:
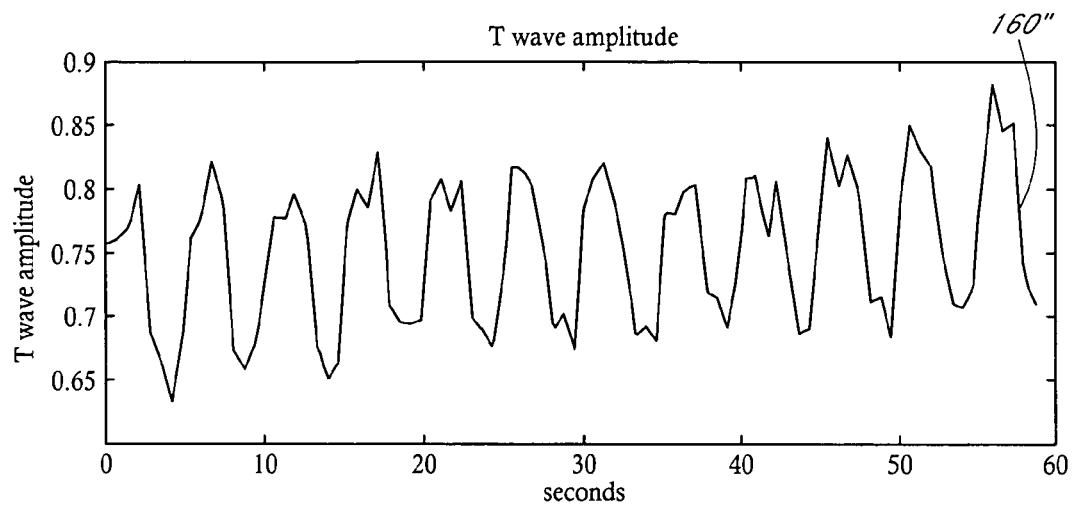

FIGS. 7A, 7B, and 7C illustrate additional embodiments of cardiac-based respiration indicators which can be utilized to determine a phase of respiration. More particularly, FIG. 7A illustrates a second cardiac-based respiration indicator 160' in this embodiment comprising variations in P-wave amplitude. FIG. 7B illustrates a third cardiac-based respiration indicator 160" in this embodiment corresponding to variations in QRS amplitude. Similarly, FIG. 7C illustrates a fourth cardiac-based respiration indicator 160''' in this embodiment corresponding to variations in T-wave amplitude. The embodiments illustrated in FIGS. 7A, 7B, and 7C offer similar advantages for implementation as for the previously described embodiments of the first cardiac-based respiration indicator 160 comprising a PDI calculation as ongoing monitoring of P-wave amplitude, QRS amplitude, and T-wave amplitude would generally already be performed by the device 10 for other purposes. In certain preferred embodiments, the device 10 conducts ongoing monitoring of the patient's cardiac activity for identification of arrhythmia conditions and thus the base signals utilized for generation of the second, third, and/or fourth cardiac-based respiration indicators 160', 160", and 160''' are already available in the device 10.

Figure 8:
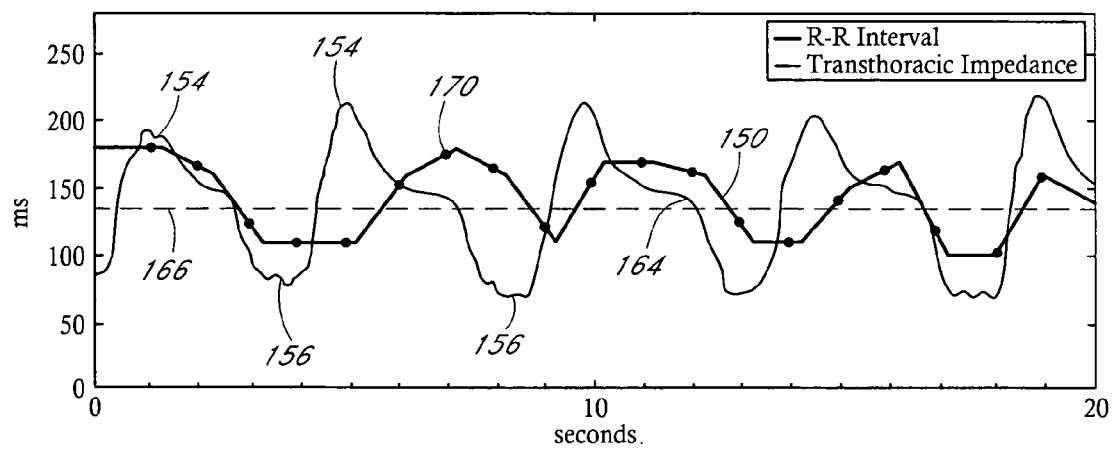
FIG. 8 illustrates one embodiment of monitoring respiration and modulating at least one cardiac therapy timing parameter.

FIG. 8 illustrates yet another embodiment of modulation of a cardiac timing characteristic 160 in concert with variations of the respiration cycle. More particularly, in this embodiment, a first cardiac timing characteristic corresponding to R-R interval (see also FIG. 3A) is actively modulated by the device 10 to track variations in the patient's respiration. In this embodiment, monitoring of the patient's respiration proceeds at least partly based on a respiration indicator 164 comprising a transthoracic impedance measurement. The respiration indicator 164 comprising a transthoracic impedance measurement monitors the time varying electrical impedance across portions of the patient's chest or thorax which cyclically vary with the filling and emptying of the lungs throughout respiration. Transthoracic measurement capability is also a relatively common feature included in implantable cardiac stimulation devices and their implementation and operation is well understood by one of ordinary skill.

In this embodiment, following the ongoing monitoring of the patient's respiration as indicated at least partially by the respiration indicator 164, the device 10 actively modulates one or more cardiac therapy timing characteristics 150 as illustrated in FIG. 8. In one particular embodiment, this modulation is performed in a quasi-real time or beat-by-beat manner such that the one or more cardiac therapy timing characteristics 150 are modulated for each cardiac cycle as indicated by the plurality of individual values 170 falling along the cardiac therapy timing characteristic curve 150. In various embodiments, the individual values 170 of the cardiac timing characteristic 150 are selected based at least partially on the indicated value of the respiration indicator 164 in a look-up table implementation. In other embodiments, the individual values 170 can be determined in a function-based manner. In one particular embodiment, the individual values 170 are determined as additives to a median value 166 during periods of exhalation phase 154 or respiration and as subtractive values from the median value 166 during inhalation phases 156 of the respiration.

Figure 9:
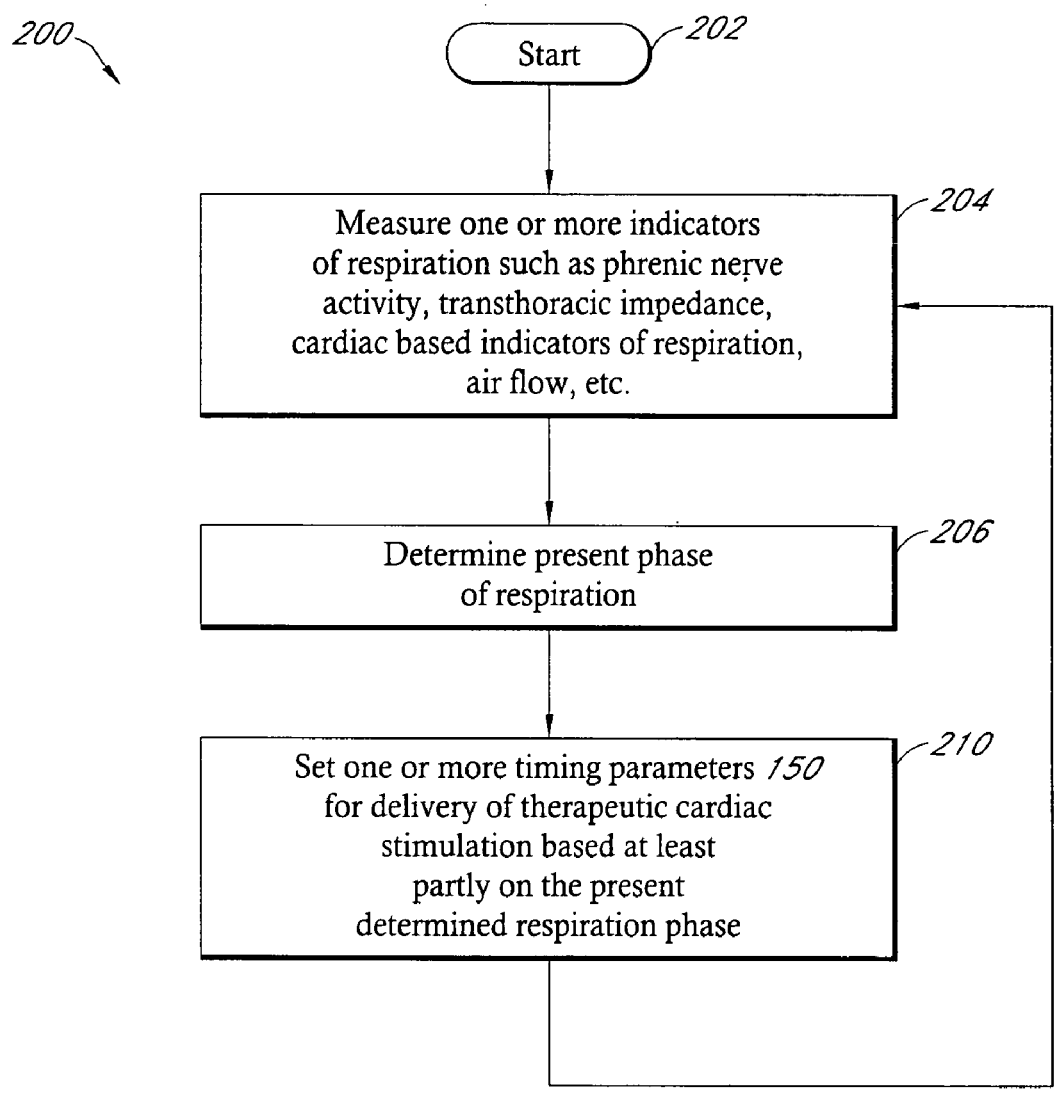
FIG. 9 is a flow chart of one embodiment of a system and method of modulating delivery of cardiac stimulation therapy with respiration phase.

FIG. 9 is a flow chart of a method 200 of modulating one or more cardiac stimulating timing characteristics 150 according to certain embodiments of the device 10 as previously described. The method 200 proceeds from a start state 202. The start state 202 includes the initial manufacture, implantation, and programming of the device 10, as well as the ongoing operation of the device 10, for example, with respect to sensing of the patient's cardiac activity and selective provision of indicated therapeutic stimulation. It should be understood that the method 200 would generally proceed in parallel with the other operations and functions of the device 10 as previously described.

Following from the start state 202 is a state 204, wherein one or more indicators of the patient's respiration are measured. In various embodiments, the measurement of state 204 can include one or more of monitoring of phrenic nerve activity, measurement of transthoracic impedance, measurement of one or more cardiac-based respiration indicators, direct measurement of air flow, such as nasal air flow, etc. Proceeding from the measurement state 204, a state 206 follows wherein the present phase of respiration, such as an exhalation phase 154 or inhalation phase 156, is determined. Following the determination of state 206, a state 210 follows wherein one or more parameters for delivery of therapeutic cardiac stimulation are set based at least partially on the present determined respiration phase from state 206. Following the setting of the one or more parameters 150 in state 210, the method returns to the measurement of state 204. The period or interval of iteration of the method 200 can vary depending on the requirements of a particular application, however in certain preferred embodiments, proceeds on a beat-by-beat basis, e.g., for each iteration of the cardiac cycle. Thus, in certain preferred embodiments, the method 200 is repeated in an iterative manner for each cardiac cycle, and the setting of the one or more parameters 150 of state 210 proceeds in an empirical manner following from the measurement of state 204 and the determination of state 206.

Figure 10:
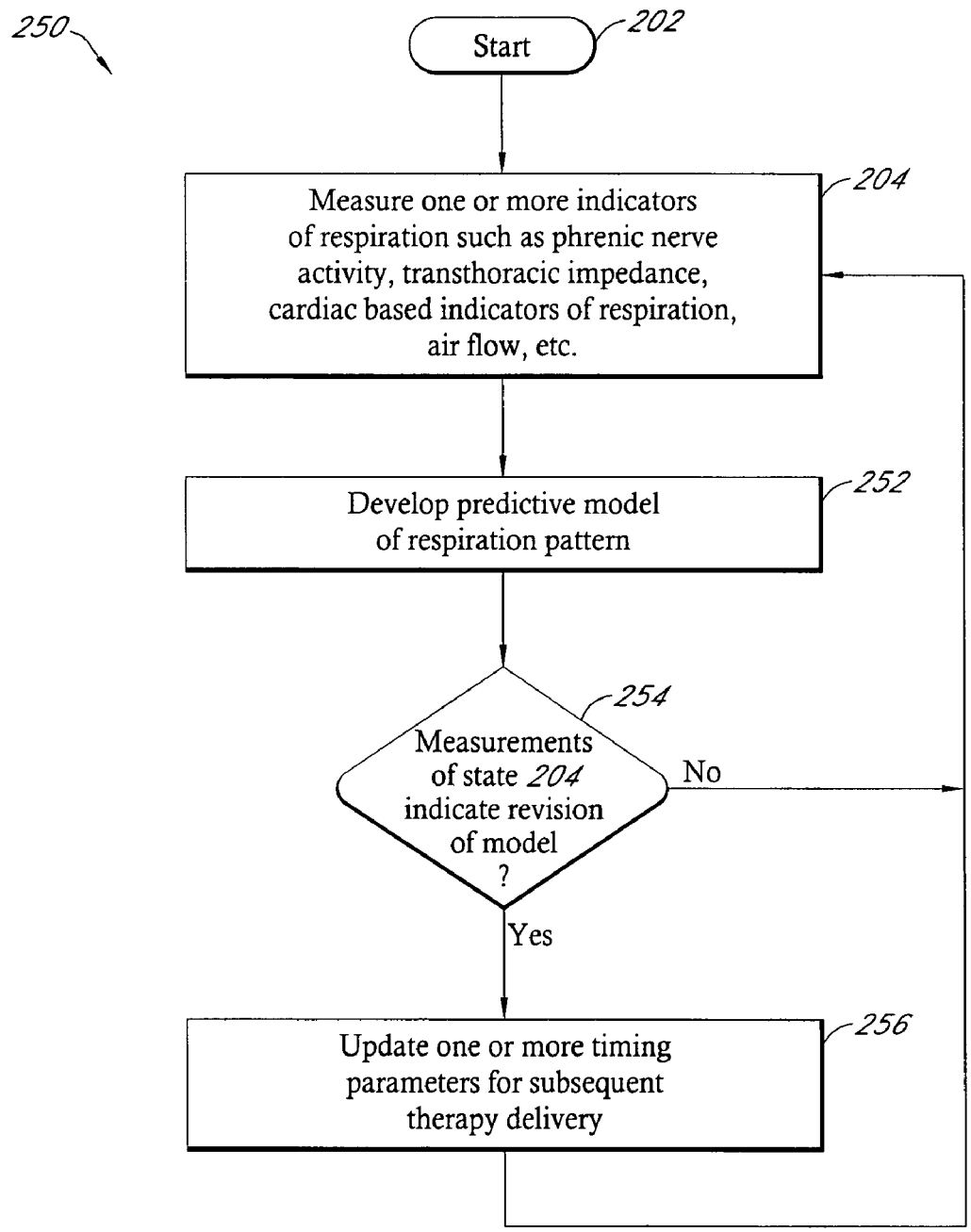
FIG. 10 is a flow chart of another embodiment of a system and method of modulating delivery of cardiac stimulation therapy with respiration phase.

FIG. 10 illustrates another embodiment of a method 250 of modulating one or more cardiac timing characteristics or parameters 150 based at least partially on patient respiration. Similarly to the method 200, the method 250 begins with a start state 202 followed by a measurement state 204 proceeding substantially identically as previously described for the method 200. Following is a state 252 wherein a predictive model of the patient's respiration pattern is developed. The patient's respiration would be normally expected to follow a generally predictable or cyclical pattern and can thus often be relatively accurately predicted on a short term basis.

As the patient's cyclical respiration and variation of the one or more cardiac timing characteristics 150 meet the required conditions of continuity and a finite number of maxima and minima, in one embodiment, the development of a predictive model of state 252 comprises a finite Fourier series. As the one or more cardiac therapy timing characteristics 150 cyclically oscillate about a median value 166, in one embodiment, the variation of the one or more cardiac timing characteristics 150 can be modeled as $$c + \sum_{n=1}^{N} a_n \sin n\omega.$$

The number of terms N in the series can be selected based on the desired degree of convergence as well as the available processing and speed capabilities of a particular application, however, generally a value of N of 10 or less will give more than satisfactory results.

The predictive model developed in state 252 is then utilized to modulate the one or more cardiac characteristics 150 and this would preferably be done on a beat-by-beat basis. Following from the modeling state 252 is a decision state 254, wherein a determination is made whether the ongoing measurements of state 204 indicate a revision of the model developed in state 252. For example, one or more characteristics of the patient's respiration, for example, depth and/or rate, may change indicating a corresponding change in the predictive model developed in state 252. If such a revision is indicated by the decision of state 254, the model is updated in a state 256 in accordance with the more recent measurements from state 204. If the determination of state 254 is negative, e.g., that the existing predictive model is satisfactory for the existing conditions, the method 250 proceeds with at least periodic measurement of the state 204 and ongoing modulation of the one or more cardiac timing characteristics 150 according to the existing predictive model from state 252. Thus, the method 250 also modulates one or more of the cardiac characteristics 150, however, in a predictive manner based upon empirically determined data rather than directly on empirically derived data as in the method 200.

Thus, various embodiments of the methods 200, 250, as well as the device 10, offer the capability of more accurately and precisely mimicking or emulating intrinsic variations in the patient's cardiac activity which may be absent, partially impaired, and/or suppressed or overridden by the therapy provided by the device 10. The improved methods of treatment provided by the device 10 can be advantageously implemented at relatively low cost and effort as certain embodiments take advantage of already existing measurements or sensed signals which are utilized for other functions in the device 10, thereby reducing the additional overhead to implement certain of the previously described embodiments. In one particular embodiment, the device 10 and methods of treatment 200, 250 can provide a patient experiencing partial or total AV block with cardiac stimulation therapy which more naturally emulates natural intrinsic AV conduction which, in certain applications, provides improved hemodynamic performance for the patient when treated according to one or more of the previously described embodiments of the invention.

Although the above disclosed embodiments of the present teachings have shown, described and pointed out the fundamental novel features of the invention as applied to the above-disclosed embodiments, it should be understood that various omissions, substitutions, and changes in the form of the detail of the devices, systems and/or methods illustrated may be made by those skilled in the art without departing from the scope of the present teachings. Consequently, the scope of the invention should not be limited to the foregoing description but should be defined by the appended claims.

What is claimed is:

1. An implantable cardiac stimulation device comprising:
    an implantable stimulation pulse generator;
    at least one implantable stimulation electrode connected to the stimulation pulse generator;
    at least one implantable sensing electrode arranged to sense cardiac electrical activity; and
    a controller receiving cardiac electrical activity signals from the at least one sensing electrode wherein the controller is in communication with the pulse generator so as to selectively induce the pulse generator to provide indicated therapeutic cardiac stimulations via the at least one stimulation electrode according to one or more therapy parameters and wherein the controller evaluates cardiac electrical activity signals sensed by the at least one implantable sensing electrode and utilizes a series of polarization amplitudes within the signals as a cardiac based respiration indicator to monitor cyclical variations corresponding to respiration and wherein at least one of the parameters comprises an interval and wherein the interval is varied such that it is elongated during expiration phases of respiration and shortened during inspiration phases of respiration.

2. The implantable cardiac stimulation device of claim 1, comprising a plurality of sensing and stimulation electrodes arranged to provide sensing from and therapeutic stimulation to multiple heart chambers and wherein the interval comprises a delay between sensing of an intrinsic event or an evoked response in a first chamber and delivery of therapeutic stimulation to a second chamber.

3. The implantable cardiac stimulation device of claim 1 wherein the polarization amplitude comprises at least one of P-wave amplitude, QRS-wave amplitude and T-wave amplitude.

4. The implantable cardiac stimulation device of claim 1 wherein the interval is varied for each of a cardiac cycle based on the respiration phase derived directly from the cardiac signals received for the particular cardiac cycle.

5. The implantable cardiac stimulation device of claim 1 wherein the interval is varied for each of a cardiac cycle based on the respiration phase determined from a predictive model that is derived from cardiac signals received over time.

6. The implantable cardiac stimulation device of claim 5 wherein the controller monitors the respiration pattern to determine if the predictive model needs to be revised.

7. An implantable cardiac stimulation device comprising:
    means for sensing cardiac electrical activity using at least on implantable sensing electrode;
    means for generating and delivering stimulation to patient tissue; and means for evaluating cardiac electrical activity signals sensed by the at least one implantable sensing electrode and utilizing a series of polarization amplitudes within the signals as a cardiac based respiration indicator to monitor cyclical variations corresponding to respiration; and means for controlling timing of delivery of the stimulation according to one or more therapy parameters based at least in part on the cardiac based respiration indicator, wherein the parameters comprise a timing parameter and wherein the controller modulates the parameters with the respiration by extending the timing parameter during exhalation phases and shortening the timing parameter during inspiration phases.

8. The device of claim 7, wherein the means for controlling determines the respiration phase based at least in part on sensed evoked responses following stimulation provided by the means for generating and delivering stimulation.

* * * * *